(12) United States Patent
West

(10) Patent No.: US 7,470,665 B2
(45) Date of Patent: Dec. 30, 2008

(54) METHODS FOR TARGETING CELLS THAT EXPRESS FIBROBLAST GROWTH RECEPTOR-3 OR -2

(75) Inventor: James W. West, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 493 days.

(21) Appl. No.: 10/354,859

(22) Filed: Jan. 29, 2003

(65) Prior Publication Data
US 2003/0152568 A1     Aug. 14, 2003

Related U.S. Application Data

(63) Continuation of application No. 09/724,240, filed on Nov. 28, 2000, now abandoned.

(60) Provisional application No. 60/168,516, filed on Dec. 2, 1999.

(51) Int. Cl.
*A61K 38/18* (2006.01)
*C07K 14/50* (2006.01)
*C07K 14/415* (2006.01)
*C07K 19/00* (2006.01)

(52) U.S. Cl. .................. 514/12; 530/350; 530/370

(58) Field of Classification Search ................ None
See application file for complete search history.

(56) References Cited

U.S. PATENT DOCUMENTS

| | | | |
|---|---|---|---|
| 5,116,753 A | 5/1992 | Beattie et al. | 435/240.2 |
| 5,191,067 A | 3/1993 | Lappi et al. | 530/399 |
| 5,308,622 A | 5/1994 | Casscells et al. | 424/422 |
| 5,478,804 A | 12/1995 | Calabresi et al. | 514/2 |
| 5,576,288 A | 11/1996 | Lappi et al. | 514/2 |
| 5,679,637 A | 10/1997 | Lappi et al. | 514/2 |
| 5,916,772 A | 6/1999 | Lappi et al. | 435/69.7 |
| 5,989,866 A | 11/1999 | Deisher et al. | 435/69.4 |

FOREIGN PATENT DOCUMENTS

| | | |
|---|---|---|
| WO | WO90/12597 | 11/1990 |
| WO | WO97/23510 | 7/1997 |
| WO | WO98/16644 | 4/1998 |

OTHER PUBLICATIONS

Szebenyi et al. Fibroblast growth factors as multifunctional signaling factors. Int Rev Cytol. 185:45-106. Sep. 3, 1998.*
Schweigerer et al. Basic fibroblast growth factor as a growth inhibitor for cultured human tumor cells. J Clin Invest. Nov. 1987; 80(5):1516-20.*
Bowie et al. Deciphering the message in protein sequences: tolerance to amino acid substitutions. Science, (Mar. 16, 1990) 247 (4948) 1306-10.*
Ngo et al., The Protein Folding Problem and Tertiary Structure Prediction, Merz and Le Grand (Eds), Aug. 1994, Springer Verlag, pp. 433 and 492-495.*
Chesi, M., Nardini, E., Lim, R.S., Smith, K.D., Kuehl, W.M., and Bergsagel, P.L., "The t(4;14) translocation in myeloma dysregulates both FGFR3 and a novel gene . . . ," *Blood* 92(9):3025-3034 (Nov. 1, 1998).
Coll-Fresno, P.M., Batoz, M., Tarquin, S., Bimbaum, D., and Coulier, F., "Cytotoxic activity of a diptheria toxin/FGF6 mitotoxin on human tumour cell lines," *Oncogene* 14(2):243-247 (Jan. 16, 1997).
Hu, M.C.-T., Qiu, W.R., Wang, Y.-P., Hill, D., et al., "FGF-18, a novel member of the fibroblast growth factor family, stimulates hepatic . . . ," *Molecular and Cellular Biology* 18(10):6063-6074 (Oct. 1998).
Hu, M.C.-T., Wang, Y.-P., and Qiu, W.R., "Human fibroblast growth factor-18 stimulates fibroblast cell proliferation and is mapped to chromosome 14p11," *Oncogene* 18:2635-2642 (Apr. 22, 1999).
Lappi, D.A., Martineau, D., and Baird, A., "Biological and chemical characterization of basic FGF-saporin mitotoxin," *Biochemical and Biophysical Research Communincations* 160(2):917-923 (Apr. 28, 1989).
Lappi, D.A., "Tumor targeting through fibroblast growth factor receptors," *Seminars in Cancer Biology* 6:279-288 (1995).
Lin, P.H., Ren, D., Hirko, M.K., Kang, S.S., Pierce, G.F., and Greisler, H.P., "Fibroblast growth factor-2-toxin induced cytotoxicity: differential sensitivity of co-cultured vascular . . . ," *Atherosclerosis* 137:277-289 (1998).
Ohbayashi, N., Hoshikawa, M., Kimura, S., Yamasaki, M., Fukui, S., and Itoh, N., "Structure and expression of the mRNA endoding . . . , FGF-18," *The Journal of Biological Chemistry* 273(29):18161-18164 (Jul. 17, 1998).
Shimoaka, T., Yonamine, A., Itoh, N., Kawano, H. et al., "Fibroblast growth factor (FGF)-18 is a potent regulator of osteoblasts, osteoclasts . . . ," *Journal of Bone and Mineral Research* 15:S257 (Sep. 2000).
International Search Report for application No. PCT/US00/32380. Year not needed. Aug. 27, 2008.
The Merck Manual of Diagnosis and Therapy, Beers (ed.); Whitehouse Station, N.J. 1999; pp. 466-467.

* cited by examiner

*Primary Examiner*—David S Romeo
(74) *Attorney, Agent, or Firm*—Michelle L. Lewis; Robyn Adams

(57) ABSTRACT

Fibroblast growth factor-18 (FGF-18) binds with FGF receptors-2 and -3. Compositions comprising an FGF-18 component can be used to target cells that express these receptors. Suitable targets include tumor cells that express constitutively activated forms of FGF receptors-2 and -3. For example, conjugates of FGF-18 and saporin can be used to target tumor cells that express FGF receptors-2 or -3, and to inhibit the proliferation of these cells.

17 Claims, No Drawings

METHODS FOR TARGETING CELLS THAT EXPRESS FIBROBLAST GROWTH RECEPTOR-3 OR -2

CROSS-REFERENCE TO RELATED APPLICATIONS

This application is a continuation of U.S. application Ser. No. 09/724,240, filed 28 Nov. 2000, now abandoned which claims the benefit of U.S. Provisional Application Ser. No. 60/168,516, filed 2 Dec. 1999, both of which are herein incorporated by reference.

TECHNICAL FIELD

The present invention relates generally to methods for inhibiting the proliferation of cells with a composition containing a fibroblast growth factor-18 component. In particular, the present invention relates to a method for targeting a cytotoxin to cells that express fibroblast growth factor receptor-3 or fibroblast growth factor receptor-2.

BACKGROUND OF THE INVENTION

Multiple myeloma represents the second most common hematologic malignancy, with nearly 15,000 new cases each year in the United States (Henrick et al., *Curr. Opin. Hematol.* 5:254 (1998)). The disease is characterized by the malignant proliferation of plasma cells involving more than 10% of the bone marrow (George and Sadovsky, *Am. Fam. Physician* 59:1885 (1999)). Multiple myeloma cells produce monoclonal immunoglobulins that may be identified with serum or urine protein electrophoresis. The most common clinical manifestations include bone pain, weakness, and fatigue (Kyle, *Pathol. Biol.* (Paris) 47:148 (1999)).

The standard chemotherapy for multiple myeloma was introduced more than 30 years ago, and since then, there has been little improvement in the overall survival rate (San Miguel et al., *Haematologica* 84:36 (1999)). Despite a wide variety of chemotherapeutic and supportive treatment options, multiple myeloma is almost invariably fatal (Anderson et al., *Semin. Hematol.* 36 (Suppl. 3):3 (1999)). While high-dose chemotherapy followed by stem cell transplantation produces higher remission rates, patients are rarely, if ever, cured by a single regimen (Anderson et al., *Semin. Hematol.* 36 (Suppl. 3):3 (1999)). Relapse is inevitable in all but a small number of cases, and for the majority of cases, treatment only produces, at best, periods of remission with minimal treatment-related morbidity and mortality (Smith and Newland, *QJM* 92:11 (1999)). The aggregate median survival for all stages of multiple myeloma is about three years (Henrick et al., *Curr. Opin. Hematol.* 5:254 (1998); George and Sadovsky, *Am. Fam. Physician* 59:1885 (1999)).

Accordingly, a need still exists for improved methods of treating multiple myeloma.

BRIEF SUMMARY OF THE INVENTION

The present invention provides compositions for targeting cells that express fibroblast growth factor receptor-2 or -3. The present invention also provides methods for inhibiting cell proliferation using such compositions. These and other aspects of the invention will become evident upon reference to the following detailed description. Various references are identified below and are incorporated by reference in their entirety.

DETAILED DESCRIPTION OF THE INVENTION

1. Overview

The fibroblast growth factor (FGF) family consists of at least eighteen distinct members, which generally act as mitogens for a broad spectrum of cell types (Basilico et al., *Adv. Cancer Res.* 59:115 (1992); Fernig et al., *Prog. Growth Factor Res.* 5:353 (1994)). For example, basic FGF (also known as FGF-2) is mitogenic in vitro for endothelial cells, vascular smooth muscle cells, fibroblasts, and generally for cells of mesoderm or neuroectoderm origin, including cardiac and skeletal myocytes (Gospodarowicz et al., *J. Cell. Biol.* 70:395 (1976); Gospodarowicz et al., *J. Cell. Biol.* 89:568 (1981); Kardami, *J. Mol. Cell. Biochem.* 92:124 (1990)). Various members of the FGF family also stimulate non-mitogenic effects, including increased endothelial release of tissue plasminogen activator, stimulation of extracellular matrix synthesis, chemotaxis for endothelial cells, induced expression of fetal contractile genes in cardiomyocytes, and enhanced pituitary hormonal responsiveness (Baird et al., *J. Cellular Physiol.* 5:101 (1987); Parker et al., *J. Clin. Invest.* 85:507 (1990)).

Deisher et al., international publication No. WO98/16644, described the discovery of a new nucleotide sequence that encodes an FGF homologue polypeptide that shares homology with FGF-8 and FGF-17 (Hoshikawa et al., *Biochem. Biophys. Res. Comm.* 244:187 (1998)). Sequence analysis of a cDNA molecule encoding the new FGF, designated as "zFGF5," revealed the nucleotide sequence of SEQ ID NO: 1, which includes an open reading frame encoding 207 amino acids (SEQ ID NO: 2) that comprises a mature polypeptide of 180 amino acids (residue 28 to residue 207 of SEQ ID NO: 2). Multiple alignment of zFGF5 with other known FGF polypeptides revealed a block of significant percent identity corresponding to amino acid residue Cys127 to amino acid residue Tyr138 of SEQ ID NO: 2. Analysis of the tissue distribution of the human mRNA corresponding to this novel DNA showed that expression was highest in fetal heart tissue and adult heart tissue, followed by apparent but decreased expression levels in fetal lung, skeletal muscle, smooth muscle tissues such as small intestine, colon and trachea.

A murine zFGF5 cDNA was cloned using the polymerase chain reaction with a mouse embryo cDNA library as a template and oligonucleotide primers designed from the 5' and 3' ends of the human zFGF5 cDNA (Deisher et al., international publication No. WO98/16644). The murine zFGF5 polynucleotide sequence is shown in SEQ ID NO: 3, and the corresponding amino acid sequence is shown in SEQ ID NO: 4. At the amino acid level, the murine and human polypeptides are approximately 98% identical, with the following three amino acid changes: amino acid residue 26 is valine in the human sequence and alanine in the murine sequence, amino acid residue 183 is proline in the human sequence and alanine in the murine sequence, and amino acid residue 207 is alanine in the human sequence and glycine in the murine sequence. Since the twenty-sixth amino acid residue of both sequences occurs in the secretory signal sequence, there are only two amino acid differences in the mature polypeptides.

The new form of FGF has also been described by Hu et al., *Mol. Cell. Biol.* 18:6063 (1998), Ohbayashi et al., *J. Biol. Chem.* 273:18161 (1998), and Hu et al., *Oncogene* 18:2635 (1999)). Following the FGF naming convention, these groups designated the new polypeptide as "FGF-18." Accordingly, zFGF5 is referred to as FGF-18 herein.

There are four known extracellular FGF receptors, and they are all tyrosine kinases. In general, the FGF family members bind to all of the known FGF receptors, however, specific FGF forms bind with specific receptors with higher degrees of affinity. Hu et al., *Oncogene* 18:2635 (1999), noted that is not clear whether FGF-18 binds to any known member of the FGF receptor family, or whether FGF-18 binds with a novel receptor. The present inventor has discovered that FGF-18 has a high specificity for FGF receptor-3, and a lower specificity for FGF receptor-2. FGF-18 does not bind with other members of the FGF receptor family even at relatively high concentrations of the ligand. These observations indicate that FGF-18 can be used to target cells that express FGF receptor-3, and to a lesser extent, FGF receptor-2. For example, FGF-18 can be used as a targeting moiety to screen cell banks or tissue slices for the identification of cells expressing cognate receptors. Conversely, a composition comprising an FGF-18 component and a cytotoxin can be used to remove cells expressing cognate receptors from continuous cell lines or primary tissue preparations.

As described herein, the present invention provides FGF-18 targeting compositions, comprising an FGF-18 component and a cytotoxin. Examples of FGF-18 components include FGF-18 polypeptides, and FGF-18 functional fragments. Illustrative FGF-18 polypeptides include variant FGF-18 polypeptides and FGF-18 anti-idiotype antibodies A particular example of an FGF-18 polypeptide is a polypeptide that comprises amino acid residues 28 to 207 of either SEQ ID NO: 2 or SEQ ID NO: 4. An example of an FGF-18 functional fragment is a polypeptide that comprises amino acid residues 28 to 175 of either SEQ ID NO: 2 or SEQ ID NO: 4, or amino acid residues 28 to 196 of either SEQ ID NO: 2 or SEQ ID NO: 4.

Suitable cytotoxin moieties include ribosome-inactivating proteins, immunomodulators, chemotherapeutic drugs, tyrosine kinase inhibitors, chelators, boron compounds, photoactive agents, and radioisotopes.

FGF-18 targeting compositions can comprise an FGF-18 component and cytotoxin that are covalently bound to each other. For example, an FGF-18 targeting composition can comprise an FGF-18 conjugate. One example of an FGF-18 conjugate is an FGF-18-saporin conjugate.

Alternatively, FGF-18 targeting compositions can comprise an FGF-18 targeting fusion protein. Illustrative fusion proteins include polypeptides comprising a cytotoxin selected from the group consisting of type I ribosome-inactivating protein, type II ribosome-inactivating protein, immunomodulator, ribonuclease, DNase I, Staphylococcal enterotoxin-A, diphtheria toxin, Pseudomonas exotoxin, and Pseudomonas endotoxin.

In another variation, the FGF-18 targeting composition comprises an FGF-18 targeting liposome.

The present invention also provides methods for inhibiting the proliferation of cells that express fibroblast growth factor (FGF) receptor-3 or FGF receptor-2, comprising administering a composition that comprises an FGF-18 targeting composition to the cells. For example, the administered composition can be a pharmaceutical composition, and the pharmaceutical composition is administered in a therapeutically effective amount to a subject which has a tumor, wherein the tumor is comprised of cells that express FGF receptor-3 or FGF receptor-2. Such methods can be used to inhibit cells in vitro or in vivo, including multiple myeloma cells, bladder carcinoma cells, cervix carcinoma cells, thyroid carcinoma cells, osteosarcoma cells, and intimal smooth muscle cells.

The present invention also contemplates compositions comprising an FGF-18 targeting composition and a carrier. The carrier can be a conventional organic or inorganic carrier. Examples of carriers include water, buffer solution, alcohol, propylene glycol, macrogol, sesame oil, corn oil, and the like. As an illustration, the composition can be a pharmaceutical composition and the carrier can be a pharmaceutically acceptable carrier.

Additional aspects of the present invention are described below.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule. For example, representative contigs to the polynucleotide sequence 5' ATGGAGCTT 3' are 5' AGCT-Tgagt 3' and 3' tcgacTACC 5'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993)), cyclic AMP response elements (CREs), serum response elements (SREs; Treisman, Seminars in Cancer Biol. 1:47 (1990)), glucocorticoid response elements (GREs), and binding sites for other transcription factors, such as CRE/ATF (O'Reilly et al., J. Biol. Chem. 267:19938 (1992)), AP2 (Ye et al., J. Biol. Chem. 269:25728 (1994)), SP1, cAMP response element binding protein (CREB; Loeken, Gene Expr. 3:253 (1993)) and octamer factors (see, in general, Watson et al., eds., Molecular Biology of the Gene, 4th ed. (The Benjamin/Cummings Publishing Company, Inc. 1987), and Lemaigre and Rousseau, Biochem. J. 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

"protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces FGF-18 from an expression vector.

In contrast, FGF-18 can be produced by a cell that is a "natural source" of FGF-18, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of an FGF-18 polypeptide fused with a polypeptide that binds an affinity matrix. Such a fusion protein provides a means to isolate large quantities of FGF-18 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-FGF-18 antibody, and mimics an epitope of FGF-18. For example, an FGF-18 anti-idiotype antibody binds at least one of FGR receptor-2 or FGF receptor-3.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-FGF-18 monoclonal antibody fragment binds with an epitope of FGF-18.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent, such as a cytotoxin. Naked antibodies include both polyclonal and monoclonal antibodies, as well as certain recombinant antibodies, such as chimeric and humanized antibodies.

As used herein, the term "antibody component" includes both an entire antibody and an antibody fragment.

As used herein, the term "antibody fusion protein" refers to a recombinant molecule that comprises an antibody component and an FGF-18 polypeptide component. Examples of an antibody fusion protein include a protein that comprises an FGF-18 polypeptide, and either an Fc domain or an antigen-biding region.

The term "variant FGF-18 gene" refers to nucleic acid molecules that encode a polypeptide having an amino acid sequence that is a modification of SEQ ID NO: 2. Such variants include naturally-occurring polymorphisms of FGF-18 genes, as well as synthetic genes that contain conservative amino acid substitutions of the amino acid sequence of SEQ ID NO: 2. Additional variant forms of FGF-18 genes are nucleic acid molecules that contain insertions or deletions of the nucleotide sequences described herein. A variant FGF-18 gene can be identified, for example, by determining whether the gene hybridizes with a nucleic acid molecule having the nucleotide sequence of SEQ ID NO: 1, or its complement, under stringent conditions.

Alternatively, variant FGF-18 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant FGF-18 gene or variant FGF-18 polypeptide, a variant gene or polypeptide encoded by a variant gene may be functionally characterized the ability to bind specifically to an anti- FGF-18 antibody, or with the ability to bind with FGF receptor-2 or FGF receptor-3.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, $\alpha$-globin, $\beta$-globin, and myoglobin are paralogs of each other.

An "FGF-18 polypeptide" is a polypeptide that binds at least one of FGF receptor-2 and FGF receptor-3, as exemplified by a polypeptide consisting of the amino acid sequence of SEQ ID NO: 2. As described herein, certain variants of the illustrative FGF-18 polypeptide are identified by at least one of sequence identity and nucleic acid molecule hybridization with reference to the illustrative FGF-18 polypeptide. An additional example of an FGF-18 polypeptide is an FGF-18 anti-idiotype antibody.

Within the context of this invention, an "FGF-18 functional fragment" refers to a portion of an FGF-18 polypeptide which binds with at least one of FGF receptor-2 and FGF receptor-3.

As used herein, the term "FGF-18 component" includes both an FGF-18 polypeptide and an FGF-18 functional fragment.

As used herein, a "cytotoxin" is a molecule or atom which is capable of causing the death of a cell or is capable of inhibiting the growth of a cell. Examples of cytotoxins include drugs, ribosome-inactivating proteins, immunomodulators, chelators, boron compounds, photoactive agents or dyes, radioisotopes, and the like.

As used herein, the term "immunomodulator" includes cytokines, stem cell growth factors, lymphotoxins, co-stimulatory molecules, hematopoietic factors, and synthetic analogs of these molecules. Examples of immunomodulators include tumor necrosis factor, interleukins (e.g., interleukin-1 (IL-1), IL-2, IL-3, IL-4, IL-5, IL-6, IL7, IL-8, IL-9, IL-10, IL-11, IL-12, IL-13, IL-14, IL-15, IL-16, IL-17, and IL-18), colony stimulating factors (e.g., granulocyte-colony stimulating factor and granulocyte macrophage-colony stimulating factor), interferons (e.g., interferons-$\alpha$, -$\beta$, -$\gamma$, -$\omega$, -$\epsilon$, and -$\tau$), the stem cell growth factor designated "S1 factor," erythropoietin, and thrombopoietin.

An "FGF-18 targeting composition" comprises an FGF-18 component and a cytotoxin, and binds with at least one of FGF receptor-2 and FGF receptor-3. The association between the FGF-18 component and the cytotoxin can be covalent or noncovalent. For example, the FGF-18 component-cytotoxin association in FGF-18 conjugates and FGF-18 targeting fusion proteins is covalent, while FGF-18 targeting liposomes illustrate a noncovalent association.

An "FGF-18 conjugate" is a type of FGF-18 targeting composition, which is produced by covalently linking an FGF-18 component and a cytotoxin either directly or via a linking agent.

As used herein, the term "FGF-18 targeting fusion protein" refers to a recombinant molecule that comprises an FGF-18 polypeptide component and a cytotoxin.

Due to the imprecision of standard analytical methods, molecular weights and lengths of polymers are understood to be approximate values. When such a value is expressed as "about" X or "approximately" X, the stated value of X will be understood to be accurate to ±10%.

3. Preparation of FGF-18 Components

A. Production of FGF Polypeptides

Nucleic acid molecules encoding a human FGF-18 gene can be obtained by screening a human cDNA or genomic library using polynucleotide probes based upon SEQ ID NO: 1, or sequences disclosed in references described above. These techniques are standard and well-established. See, for example, White (ed.), *Methods in Molecular Biology, Vol.* 15: *PCR Protocols: Current Methods and Applications* (Humana Press, Inc. 1993), Ausubel et al. (eds.), *Short Protocols in Molecular Biology*, 3rd Edition (John Wiley & Sons 1995) ["Ausubel (1995)"], and Wu et al., *Methods in Gene Biotechnology* (CRC Press, Inc. 1997) ["Wu (1997)"].

As an alternative, an FGF-18 gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol.* 15: *PCR Protocols: Current Methods and Applications*, White (ed.), pages 263-268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

Those skilled in the art will recognize that the sequence disclosed in SEQ ID NO: 1 represents a single allele of human FGF-18, and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO: 1, including those containing silent mutations and those in which mutations result in amino acid sequence changes, are within the scope of the present invention, as are proteins which are FGF-18 allelic variants. cDNA molecules generated from alternatively spliced mRNAs, which retain the properties of the FGF-18 polypeptide are suitable for the present invention, as are polypeptides encoded by such cDNAs and mRNAs. Allelic variants and splice variants of these sequences can be cloned by probing cDNA or genomic libraries from different individuals or tissues according to standard procedures known in the art.

FGF-18 polypeptides, including full-length polypeptides, functional fragments, and fusion proteins, can be produced in recombinant host cells following conventional techniques. To express an FGF-18 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, an FGF-18 expression vector may comprise a nucleotide sequence that encodes an polypeptide and a secretory sequence derived from any secreted gene, including FGF-18.

FGF-18 proteins of the present invention can be expressed in prokaryotic or eukaryotic cells. Illustrative prokaryotic cells include *E. coli* and *Bacillus subtilus*. Illustrative eukaryotic cells include mammalian cells, fungal cells, avian cells, yeast cells, insect cells, and plant cells. Methods for expressing proteins in recombinant host cells are well-known to those of skill in the art (see, for example, Murray (ed.), *Gene Transfer and Expression Protocols* (Humana Press 1991), Ausubel (1995), Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), Georgiou, "Expression of Proteins in Bacteria," in *Protein Engineering: Principles and Practice*, Cleland et al. (eds.), page 101 (John Wiley & Sons, Inc. 1996), and Fernandez and Hoeffler (eds.), *Gene Expression Systems: Using Nature for the Art of Expression* (Academic Press, Inc. 1999)).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems*, 2nd Edition, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, FGF-18 polypeptides of the present invention can be synthesized by exclusive solid phase synthesis, partial solid phase methods, fragment condensation or classical solution synthesis. These synthesis methods are well-known to those of skill in the art. For example, standard solid phase peptide synthesis is described by Merrifield, *J. Am. Chem. Soc.* 85:2149 (1963), and by Lloyd-Williams et al., *Chemical Approaches to the Synthesis of Peptides and Proteins* (CRC Press 1997). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

The polypeptides of the present invention can be purified to at least about 80% purity, to at least about 90% purity, to at least about 95% purity, or greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. Certain purified polypeptide preparations are substantially free of other polypeptides, particularly other polypeptides of animal origin.

Fractionation and/or conventional purification methods can be used to obtain preparations of FGF-18 purified from natural sources (e.g., heart tissue), synthetic FGF-18 polypeptides, and recombinant FGF-18 polypeptides and fusion FGF-18 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Additional variations in protein isolation and purification can be devised by those of skill in the art. For example, anti-FGF-18 antibodies, obtained as described below, can be used to isolate large quantities of protein by immunoaffinity purification.

B. Variant FGF-18 Polypeptides (1) Mutations of the Illustrative FGF-18 Polypeptide Those skilled in the art will readily recognize that, in view of the degeneracy of the genetic code, considerable sequence variation is possible among these polynucleotide molecules. As an illustration, SEQ ID NO: 5 is a degenerate nucleotide sequence that encompasses all nucleic acid molecules that encode the human FGF-18 polypeptide of SEQ ID NO: 2. Those skilled in the art will recognize that the degenerate sequence of SEQ ID NO: 5 also provides all RNA sequences encoding SEQ ID NO: 2, by substituting U for T. Thus, the present invention contemplates the production of FGF-18 polypeptide-encoding nucleic acid molecules comprising nucleotide 82 to nucleotide 621 of SEQ ID NOs: 1 or 3, and their RNA equivalents.

Table 1 sets forth the one-letter codes used within SEQ ID NO: 5 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO: 5, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO: 2 or SEQ ID NO: 4.

Different species can exhibit "preferential codon usage." In general, see, Grantham et al., *Nucl. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are FGF-18 polypeptides from other mammalian species, including porcine, ovine, bovine, canine, feline, equine, and other primate polypeptides. Orthologs of human FGF-18 can be cloned using information and compositions provided by the present invention in combination with conventional cloning techniques. This is illustrated by the cloning of the murine FGF-18. Suitable sources of mRNA can be identified by probing northern blots with probes designed from the sequences disclosed herein. A library is then prepared from mRNA of a positive tissue or cell line.

Those skilled in the art will recognize that the sequence disclosed in SEQ ID NO: 1 represents a single allele of human FGF-18, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of the FGF-18 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO: 1, to nucleic acid molecules consisting of the nucleotide sequence of nucleotides 82 to 621 of SEQ ID NO: 1, or to nucleic acid molecules comprising a nucleotide sequence complementary to SEQ ID NO: 1 or to nucleotides 82 to 621 of SEQ ID NO: 1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5-25° C. below the $T_m$ of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20-70° C. and a hybridization buffer containing up to 6×SSC and 0-50% formamide. A higher degree of stringency can be achieved at temperatures of from 40-70° C. with a hybridization buffer having up to 4×SSC and from 0-50% formamide. Highly stringent conditions typically encompass temperatures of 42-70° C. with a hybridization buffer having up to 1×SSC and 0-50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below. This allows for the maximum rate of hybridization for DNA-DNA and DNA-RNA hybrids.

The length of the polynucleotide sequence influences the rate and stability of hybrid formation. Smaller probe sequences, less than 50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxyuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M sodium chloride, 15 mM sodium citrate) or SSPE (1×SSPE: 1.8 M NaCl, 10 mM $NaH_2PO_4$, 1 mM EDTA, pH 7.7). Typically, hybridization buffers contain from between 10 mM-1 M $Na^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant FGF-18 polypeptide can be hybridized with a nucleic acid molecule consisting of the nucleotide sequence of SEQ ID NO: 1 (or its complement) at 42° C. overnight in a solution comprising 50% formamide, 5×SSC, 50 mM sodium phosphate (pH 7.6), 5×Denhardt's solution (100×Denhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. For example, certain nucleic acid molecules encoding a variant FGF-18 polypeptide remain hybridized with a nucleic acid molecule consisting of the nucleotide sequence of SEQ ID NO: 1 (or its complement) following stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. As an illustration, particular nucleic acid molecules encoding a variant FGF-18 polypeptide remain hybridized with a nucleic acid molecule consisting of the nucleotide sequence of SEQ ID NO: 1 (or its complement) following highly stringent washing conditions, in which the wash stringency is equivalent to 0.1×-0.2×SSC with 0.1% SDS at 50-65° C. including 0.1×SSC with 0.1% SDS at 50° C., or 0.2×SSC with 0.1% SDS at 65° C.

The present invention also provides polypeptides comprising FGF-18 amino acid sequences that have a substantially similar sequence identity to the polypeptides of SEQ ID NO: 2, or their orthologs. The term "substantially similar sequence identity" is used herein to denote polypeptides having at least 70%, at least 80%, at least 90%, at least 95% or greater than 95% sequence identity to the sequences shown in SEQ ID NO: 2, or their orthologs.

The present invention also contemplates FGF-18 variant nucleic acid molecules that can be identified using two criteria: a determination of the similarity between the encoded polypeptide with the amino acid sequence of SEQ ID NO: 2, and a hybridization assay, as described above. Such FGF-18 variants include nucleic acid molecules (1) that remain hybridized with a nucleic acid molecule consisting of the nucleotide sequence of SEQ ID NO: 1 (or its complement) following stringent washing conditions, in which the wash stringency is equivalent to 0.5×-2×SSC with 0.1% SDS at 55-65° C., and (2) that encode a polypeptide having at least 70%, at least 80%, at least 90%, at least 95% or greater than 95% sequence identity to the amino acid sequence of SEQ ID NO: 2. Alternatively, FGF-18 variants can be characterized as nucleic acid molecules (1) that remain hybridized with a nucleic acid molecule consisting of the nucleotide sequence of SEQ ID NO: 1 (or its complement) following highly stringent washing conditions, in which the wash stringency is equivalent to 01×-0.2×SSC with 0.1% SDS at 50-65° C., and (2) that encode a polypeptide having at least 70%, at least 80%, at least 90%, at least 95% or greater than 95% sequence identity to the amino acid sequence of SEQ ID NO: 2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative FGF-18 variant. The FASTA algorithm is described by Pearson and Lipman, Proc Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO: 2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with an amino acid sequence disclosed herein. For example, variants can be obtained that contain one or more amino acid substitutions of SEQ ID NO: 2, in which an alkyl amino acid is substituted for an alkyl amino acid in an FGF-18 amino acid sequence, an aromatic amino acid is substituted for an aromatic amino acid in an FGF-18 amino acid sequence, a sulfur-containing amino acid is substituted for a sulfur-containing amino acid in an FGF-18 amino acid sequence, a hydroxy-containing amino acid is substituted for a hydroxy-containing amino acid in an FGF-18 amino acid sequence, an acidic amino acid is substituted for an acidic amino acid in an FGF-18 amino acid sequence, a basic amino acid is substituted for a basic amino acid in an FGF-18 amino acid sequence, or a dibasic monocarboxylic amino acid is substituted for a dibasic monocarboxylic amino acid in an FGF-18 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. As an illustration, a conservative amino acid substitution of dibasic amino acid residues can be introduced at amino acid residues 196 and 197of SEQ ID NO: 2 or SEQ ID NO: 4.

The BLOSUM62 table is an amino acid substitution matrix derived from about 2,000 local multiple alignments of protein sequence segments, representing highly conserved regions of more than 500 groups of related proteins (Henikoff and Henikoff, Proc Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than -1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of FGF-18 are characterized by having at least 70%, at least 80%, at least 90%, at least 95% or greater than 95% sequence identity to the corresponding amino acid sequence (e.g., SEQ ID NO: 2), wherein the variation in amino acid sequence is due to one or more conservative amino acid substitutions.

Conservative amino acid changes in an FGF-18 gene can be introduced, for example, by substituting nucleotides for the nucleotides recited in SEQ ID NO: 1. Such "conservative amino acid" variants can be obtained by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). A variant FGF-18 polypeptide can be identified by the ability to specifically bind anti-FGF-18 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for FGF-18 amino acid residues. For example, alanine mutations can be introduced into the polypeptide (see, for example, Hilton et al., *J. Biol. Chem.* 271:4699 (1996)).

Variants of the disclosed FGF-18 nucleotide and polypeptide sequences can also be generated through DNA shuffling as disclosed by Stemmer, *Nature* 370:389 (1994), Stemmer, *Proc Nat'l Acad. Sci. USA* 91:10747 (1994), and international publication No. WO97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-FGF-18 antibodies, can be recovered from the host cells and rapidly sequenced using modern equipment. These methods allow the rapid determination of the importance of individual amino acid residues in a polypeptide of interest, and can be applied to polypeptides of unknown structure.

(2) FGF-18 Anti-idiotype antibodies

Anti-idiotype antibodies provide another form of FGF-18 variant polypeptide. Since the variable domains of anti-idiotype FGF-18 antibodies mimic FGF-18, these domains can also provide FGF-18 receptor binding activity. Those of skill in the art are aware that recombinant antibodies comprising anti-idiotype variable domains are useful as analogs (see, for example, Monfardini et al., *Proc. Assoc. Am. Physicians* 108: 420 (1996)). These anti-idiotype antibodies are produced from anti-FGF-18 antibodies, using standard techniques.

Antibodies to FGF-18 can be obtained, for example, following methods described by Deisher et al., international publication No. WO98/16644. For example, polyclonal antibodies to recombinant FGF-18 protein or to FGF-18 isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995). The immunogenicity of an FGF-18 polypeptide can be increased through the use of an adjuvant, such as alum (aluminum hydroxide) or Freund's complete or incomplete adjuvant. Polypeptides useful for immunization also include fusion polypeptides, such as fusions of FGF-18 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin, bovine serum albumin, or tetanus toxoid, etc.) for immunization.

Although polyclonal antibodies are typically raised in animals such as horses, cows, dogs, chicken, rats, mice, rabbits, guinea pigs, goats, or sheep, an anti-FGF-18 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-FGF-18 antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology, Vol.* 1, pages 2.5.1-2.6.7 (John Wiley & Sons 1991) ["Coligan"], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)). Briefly, monoclonal antibodies can be obtained by injecting mice with a composition comprising an FGF-18 gene product, verifying the presence of antibody production by removing a serum sample, removing the spleen to obtain B-lymphocytes, fusing the B-lymphocytes with myeloma cells to produce hybridomas, cloning the hybridomas, selecting positive clones-which produce antibodies to the antigen, culturing the clones that produce antibodies to the antigen, and isolating the antibodies from the hybridoma cultures.

In addition, an anti-FGF-18 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology, Vol.* 10, pages 79-104 (The Humana Press, Inc. 1992)).

For particular uses, it may be desirable to prepare fragments of anti-FGF-18 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology Vol.* 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains, which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, an scFV can be obtained by exposing lymphocytes to FGF-18 polypeptide in vitro, and selecting antibody display libraries in phage or similar vectors (for instance, through use of immobilized or labeled FGF-18 protein or peptide). Genes encoding polypeptides having potential FGF-18 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides, which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the FGF-18 sequences disclosed herein to identify proteins, which bind to FGF-18.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-FGF-18 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc Nat'l Acad. Sci. USA* 86:3833 (1989). Techniques for producing humanized monoclonal antibodies are described, for example, by Jones et al., *Nature* 321:522 (1986), Carter et al., *Proc Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et al., U.S. Pat. No. 5,693,762 (1997).

Polyclonal anti-idiotype antibodies can be prepared by immunizing animals with anti-FGF-18 antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-FGF-18 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

C. FGF-18 Functional Fragments

The present invention also includes the use of "functional fragments" of FGF-18 polypeptides and nucleic acid molecules encoding such functional fragments. Routine deletion analyses of nucleic acid molecules can be performed to obtain functional fragments of a nucleic acid molecule that encodes an FGF-18 polypeptide. As an illustration, DNA molecules having the nucleotide sequence of SEQ ID NO: 1 can be digested with Bal31 nuclease to obtain a series of nested deletions. The fragments are then inserted into expression vectors in proper reading frame, and the expressed polypeptides are isolated and tested for the ability to bind anti-FGF-18 antibodies. One alternative to exonuclease digestion is to use oligonucleotide-directed mutagenesis to introduce deletions or stop codons to specify production of a desired fragment. Alternatively, particular fragments of an FGF-18 gene can be synthesized using the polymerase chain reaction.

As an illustration of this general approach, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation, Vol.* 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

Analyses of human and murine FGF-18 amino acid sequences revealed a dibasic site at the C-terminus of the polypeptides (amino acid residues 196-197; Lys-Arg). Dibasic amino acid sites, such as Lys-Arg, are susceptible to cleavage by several enzymes, including, thrombin and carboxypeptidases. A C-terminally truncated polypeptide comprising an amino acid sequence as shown in SEQ ID NO: 2, from amino acid residue Glu28 to amino acid residue Lys196, was found to have biological activity. Accordingly, one example of an FGF-18 functional fragment is a polypeptide consisting of amino acid residues 1 to 196, or 28 to 196 of SEQ ID NOs: 2 or 4. Sequence analysis of the FGF family indicates that additional FGF-18 functional fragments include polypeptides consisting of amino acid residues 1 to 175, or 28 to 175 of SEQ ID NOs: 2 or 4. Other FGF-18 functional fragments can be determined by those of skill in the art using methods described above.

The present invention also contemplates functional fragments of an FGF-18 gene that have amino acid changes, compared with an amino acid sequence disclosed herein. A variant FGF-18 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant FGF-18 gene can hybridize to a nucleic acid molecule comprising a nucleotide sequence, such as SEQ ID NO: 1 or SEQ ID NO: 4.

4. Preparation of FGF-18 Targeting Compositions

A. FGF-18 Conjugates and FGF-18 Targeting Fusion Proteins

An FGF-18 targeting composition comprises an FGF-18 component and a cytotoxin. An example of a suitable polypeptide cytotoxin is a ribosome-inactivating protein. Type I ribosome-inactivating proteins are single-chain proteins, while type II ribosome-inactivating proteins consist of two nonidentical subunits (A and B chains) joined by a disulfide bond (for a review, see Soria et al., *Targeted Diagn. Ther.* 7:193 (1992)). Useful type I ribosome-inactivating proteins include polypeptides from *Saponaria officinalis* (e.g., saporin-1, saporin-2, saporin-3, saporin-6), *Momordica charantia* (e.g, momordin), *Byronia dioica* (e.g., bryodin, bryodin-2), *Trichosanthes kirilowii* (e.g., trichosanthin, trichokirin), *Gelonium multiflorum* (e.g., gelonin), *Phytolacca americana* (e.g., pokeweed antiviral protein, pokeweed antiviral protein-II, pokeweed antiviral protein-S), *Phytolacca dodecandra* (e.g., dodecandrin, Mirabilis antiviral protein), and the like. Ribosome-inactivating proteins are described, for example, by Walsh et al., U.S. Pat. No. 5,635,384.

Suitable type II ribosome-inactivating proteins include polypeptides from *Ricinus communis* (e.g., ricin), *Abrus precatorius* (e.g., abrin), *Adenia digitata* (e.g., modeccin), and the like. Since type II ribosome-inactivating proteins include a B chain that binds galactosides and a toxic A chain that depurinates adensoine, type II ribosome-inactivating protein conjugates should include the A chain. Additional useful ribosome-inactivating proteins include bouganin, clavin, maize ribosome-inactivating proteins, *Vaccaria pyramidata* ribosome-inactivating proteins, nigrine b, basic nigrine 1, ebuline, racemosine b, luffin-a, luffin-b, luffin-S, and other ribosome-inactivating proteins known to those of skill in the art. See, for example, Bolognesi and Stirpe, international publication No. WO98/55623, Colnaghi et al., international publication No. WO97/49726, Hey et al., U.S. Pat. No. 5,635,384, Bolognesi and Stirpe, international publication No. WO95/07297, Arias et al., international publication No. WO94/20540, Watanabe et al., *J. Biochem.* 106:6 977 (1989); Islam et al., *Agric. Biol. Chem.* 55:229 (1991), and Gao et al., *FEBS Lett.* 347:257 (1994).

Analogs and variants of naturally-occurring ribosome-inactivating proteins are also suitable for the targeting compositions described herein, and such proteins are known to those of skill in the art. Ribosome-inactivating proteins can be produced using publicly available amino acid and nucleotide sequences. As an illustration, a nucleotide sequence encoding saporin-6 is disclosed by Lorenzetti et al., U.S. Pat. No. 5,529,932, while Walsh et al., U.S. Pat. No. 5,635,384, describe maize and barley ribosome-inactivating protein nucleotide and amino acid sequences. Moreover, ribosome-inactivating proteins are also commercially available.

Another group of useful polypeptide cytotoxins include immunomodulators. FGF-18 targeting compositions that include an immunomodulator provide a means to deliver an immunomodulator to a target cell and are particularly useful against tumor cells. The cytotoxic effects of immunomodulators are well known to those of skill in the art. See, for example, Klegerman et al., "Lymphokines and Monokines," in *Biotechnology And Pharmacy*, Pessuto et al. (eds.), pages 53-70 (Chapman & Hall 1993). As an illustration, interferons can inhibit cell proliferation by inducing increased expression of class I histocompatibility antigens on the surface of various cells and thus, enhance the rate of destruction of cells by cytotoxic T lymphocytes. Furthermore, tumor necrosis factors, such as tumor necrosis factor-α, are believed to produce cytotoxic effects by inducing DNA fragmentation.

Additional polypeptide cytotoxins include ribonuclease, DNase I, Staphylococcal enterotoxin-A, diphtheria toxin, Pseudomonas exotoxin, and Pseudomonas endotoxin. See, for example, Pastan et al., *Cell* 47:641 (1986), and Goldenberg, C A—*A Cancer Journal for Clinicians* 44:43 (1994). Other suitable toxins are known to those of skill in the art.

Conjugates of cytotoxic polypeptides and FGF-18 components can be prepared using standard techniques for conjugating polypeptides. For example, methods of conjugating FGF with saporin are described by Lappi et al., *Biochem. Biophys. Res. Commun.* 160:917 (1989), Soria et al., *Targeted Diagn. Ther.* 7:193 (1992), Buechler et al., *Eur. J. Biochem.* 234:706 (1995), Behar-Cohen et al., *Invest. Ophthalmol. Vis. Sci*. 36:2434 (1995), Lappi and Baird, U.S. Pat. No. 5,191,067, Calabresi et al., U.S. Pat. No. 5,478,804, and Lappi and Baird, U.S. Pat. No. 5,576,288. Additional approaches to conjugating polypeptide are known to those of skill in the art. For example, Lam and Kelleher, U.S. Pat. No. 5,055,291, describe the production of antibodies conjugated with either diphtheria toxin fragment A or ricin toxin.

FGF-18 targeting fusion proteins can also be produced using standard techniques. As an illustration, FGF-saporin recombinant proteins are described by Lappi et al., *J. Biol. Chem.* 269:12552 (1994), Behar-Cohen et al., *Invest. Ophthalmol. Vis. Sci*. 36:2434 (1995), McDonald et al., *Protein Expr. Purif.* 8:97 (1996), and Lappi et al., U.S. Pat. No. 5,916,772. In a similar manner, Landgraf et al., *Biochemistry* 37:3220 (1998), produced a fusion protein comprising an epidermal growth factor moiety and diphtheria toxin. Methods of preparing fusion proteins comprising a cytotoxic polypeptide moiety are well-known in the art of antibody-toxin fusion protein production. For example, antibody-Pseudomonas exotoxin A fusion proteins have been described by Chaudhary et al., *Nature* 339:394 (1989), Brinkmann et al., *Proc Nat'l Acad. Sci. USA* 88:8616 (1991), Batra et al., *Proc Nat'l Acad. Sci. USA* 89:5867 (1992), Friedman et al., *J. Immunol*. 150:3054 (1993), Wels et al., *Int. J. Can*. 60:137 (1995), Fominaya et al., *J. Biol. Chem*. 271:10560 (1996), Kuan et al., *Biochemistry* 35:2872 (1996), and Schmidt et al., *Int. J. Can*. 65:538 (1996). Antibody-toxin fusion proteins containing a diphtheria toxin moiety have been described by Kreitman et al., *Leukemia* 7:553 (1993), Nicholls et al., *J. Biol. Chem*. 268:5302 (1993), Thompson et al., *J. Biol. Chem*. 270:28037 (1995), and Vallera et al., *Blood* 88:2342 (1996). Deonarain et al., *Tumor Targeting* 1:177 (1995), have described an antibody-toxin fusion protein having an RNase moiety, while Linardou et al., *Cell Biophys*. 24-25:243 (1994), produced an antibody-toxin fusion protein comprising a DNase I component. Gelonin was used as the toxin moiety in the antibody-toxin fusion protein of Better et al., *J. Biol. Chem*. 270:14951 (1995). As a further example, Dohlsten et al., *Proc Nat'l Acad. Sci. USA* 91:8945 (1994), reported an antibody-toxin fusion protein comprising Staphylococcal enterotoxin-A. In addition, antibody fusion proteins comprising an interleukin-2 moiety are described by Boleti et al., *Ann. Oncol*. 6:945 (1995), Nicolet et al., *Cancer Gene Ther*. 2:161 (1995), Becker et al., *Proc Nat'l Acad. Sci. USA* 93:7826 (1996), Hank et al., *Clin. Cancer Res*. 2:1951 (1996), and Hu et al., *Cancer Res*. 56:4998 (1996), while Yang et al., *Hum. Antibodies Hybridomas* 6:129 (1995), describe a fusion protein that includes an $F(ab')_2$ fragment and a tumor necrosis factor-α moiety. These approaches can be used to prepare the FGF-18 targeting fusion proteins described herein.

As an alternative to a polypeptide cytotoxin, FGF-18 targeting compositions can comprise a radioisotope as the cytotoxin moiety. For example, an FGF-18 targeting composition can comprise an α-emitting radioisotope, a β-emitting radioisotope, a γ-emitting radioisotope, an Auger electron emitter, a neutron capturing agent that emits α-particles or a radioisotope that decays by electron capture. Suitable radioisotopes include $^{198}Au$, $^{199}Au$, $^{32}P$, $^{33}P$ $^{125}I$, $^{131}I$, $^{123}I$, $^{90}Y$, $^{186}Re$, $^{188}Re$, $^{67}Cu$, $^{211}At$, $^{47}Sc$, $^{103}Pb$, $^{109}Pd$, $^{212}$ Pb, $^{71}Ge$, $^{77}As$, $^{105}Rh$, $^{113}Ag$, $^{119}Sb$, $^{121}Sn$, $^{131}Cs$, $^{143}Pr$, $^{161}Tb$, $^{177}Lu$, $^{191}Os$, $^{193M}Pt$, $^{197}Hg$, and the like.

A radioisotope can be attached to an FGF-18 component directly or indirectly, via a chelating agent. For example, $^{67}Cu$, considered one of the more promising radioisotopes for radioimmunotherapy due to its 61.5 hour half-life and abundant supply of β-particles and γ-rays, can be conjugated to an FGF-18 component using the chelating agent, p-bromoacetamido-benzyl-tetraethylaminetetraacetic acid. Chase and Shapiro, "Medical Applications of Radioisotopes," in Gennaro (ed.), *Remington's Pharmaceutical Sciences*, 19th Edition, pages 843-865 (Mack Publishing Company 1995). As an alternative, $^{90}Y$, which emits an energetic β-particle, can be coupled to an FGF-18 component using diethylenetriaminepentaacetic acid. Moreover, an exemplary suitable method for the direct radiolabeling of an FGF-18 component with $^{131}$ I is described by Stein et al., *Antibody Immunoconj. Radiopharm*. 4:703 (1991). Alternatively, boron addends such as carboranes can be attached to FGF-18 components, using standard techniques.

Another type of suitable cytotoxin for the preparation of FGF-18 conjugates is a chemotherapeutic drug. Illustrative chemotherapeutic drugs include nitrogen mustards, alkyl sulfonates, nitrosoureas, triazenes, folic acid analogs, pyrimidine analogs, purine analogs, antibiotics, epipodophyllotoxins, platinum coordination complexes, and the like. Specific examples of chemotherapeutic drugs include methotrexate, doxorubicin, daunorubicin, cytosinarabinoside, cis-platin, vindesine, mitomycin, bleomycin, melphalan, chlorambucil, and the like. Suitable chemotherapeutic agents are described in *Remington's Pharmaceutical Sciences*, 19th Ed. (Mack Publishing Co. 1995), and in *Goodman And Gilman's The Pharmacological Basis Of Therapeutics*, 7th Ed. (MacMillan Publishing Co. 1985). Other suitable chemotherapeutic agents are known to those of skill in the art.

In another approach, FGF-18 conjugates are prepared conjugating photoactive agents or dyes to an FGF-18 component. Fluorescent and other chromogens, or dyes, such as porphyrins sensitive to visible light, have been used to detect and to treat lesions by directing the suitable light to the lesion. This type of "photoradiation," "phototherapy," or "photodynamic" therapy is described, for example, by Mew et al., *J. Immunol.* 130:1473 (1983), Jori et al. (eds.), *Photodynamic Therapy Of Tumors And Other Diseases* (Libreria Progetto 1985), Oseroff et al., *Proc. Natl. Acad. Sci. USA* 83:8744 (1986), van den Bergh, *Chem. Britain* 22:430 (1986), Hasan et al., *Prog. Clin. Biol. Res.* 288:471 (1989), Tatsuta et al., *Lasers Surg. Med.* 9:422 (1989), and Pelegrin et al., *Cancer* 67:2529 (1991).

Another general type of useful cytotoxin is a tyrosine kinase inhibitor. As described above, certain disease states are associated with a mutant FGF receptor-3 which is constitutively active. This increased signaling can cause excessive proliferation and metastasis. Since the activation of proliferation by tyrosine kinases, such as FGF receptor tyrosine kinase, has been suggested to play a role in the development and progression of tumors, this activation can be inhibited by FGF-18 components that deliver tyrosine kinase inhibitors. Suitable tyrosine kinase inhibitors include isoflavones, such as genistein (5, 7, 4'-trihydroxyisoflavone), daidzein (7,4'-dihydroxyisoflavone), and biochanin A (4-methoxygenistein), and the like. Methods of conjugating tyrosine inhibitors to a growth factor are described, for example, by Uckun, U.S. Pat. No. 5,911,995.

The present invention also includes FGF-18 targeting compositions that comprise a nucleic acid molecule encoding a cytotoxin. For example, Hoganson et al., *Human Gene Ther.* 9:2565 (1998), describe FGF-2 mediated delivery of a saporin gene by producing an FGF-2-polylysine conjugate which was condensed with an expression vector comprising a saporin gene.

B. FGF-18 Targeting Liposomes

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46: 1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phosphatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881(1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.*20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.*20:259 (1997)). Polyaconitylated human serum albumin liposomes provide another approach for targeting liposomes to liver cells (Kamps et al., *Proc Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

FGF-18 targeting compositions can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). Suitable liposomes can contain a variety of moieties, such as lipid derivatives of poly(ethylene glycol) (Allen et al., *Biochim. Biophys. Acta* 1150:9 (1993)).

In addition to providing a means of delivering FGF-18 targeting compositions, liposomes can be produced to target cells expressing FGF receptor-3 or FGF receptor-2. As noted above, a ligand can be bound to a liposome surface to target cells that express a cognate receptor. Accordingly, the present invention includes liposomes comprising an FGF-18 component bound to the surface to effect delivery of encapsulated cytotoxins.

C. Assays

The ability of an FGF-18 polypeptide or FGF-18 functional fragment to bind with its cognate receptor can be determined using a biological activity assay. For example, proliferation can be measured using cultured cells. Generally, proliferative effects are seen as an increase in cell number, which may be effected by an inhibition of apoptosis, as well as by a stimulation of mitogenesis. Suitable cultured cells for a proliferation assay include cardiac fibroblasts, cardiac myocytes, skeletal myocytes, human umbilical endothelial vein cells from primary cultures. Illustrative established cell lines include NIH 3T3 fibroblast cells (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., *Proc Natl. Acad. Sci.* 89:8928 (1992)), and LNCap.FGC adenocarcinoma cells (ATCC No. CRL-1740.) Cell proliferation assays are well known in the art. Exemplary approaches include the measurement of chemosensitivity to neutral red dye (Cavanaugh et al., *Investigational New Drugs* 8:347 (1990)), incorporation of radiolabeled nucleotides (Cook et al., *Analytical Biochem.* 179:1 (1989)), incorporation of 5-bromo-2'-deoxyuridine in the DNA of proliferating cells (Porstmann et al., *J. Immunol. Methods* 82:169 (1985)), and the use of tetrazolium salts, such as in the MTT microculture tetrazolium assay (Mosmann, *J. Immunol. Methods* 65:55 (1983); Alley et al., *Cancer Res.* 48:589 (1988); Scudiero et al., *Cancer Res.* 48:4827 (1988)Marshall et al., *Growth Reg.* 5:69 (1995); Wang and Xu, *Int. J. Cancer* 75:596 (1998)).

For example, 120 cell lines, representing various tissues, were screened for sensitivity to an FGF-18 targeting composition, which had been prepared by conjugating FGF-18 to saporin. The two most sensitive cell lines, characterized by an $LD_{50}$<1 nM, were a human osteosarcoma cell line (ATCC, CRL 1543) and a rat osteosarcoma cell line, designated "UMR 106" (ATCC, CRL 1661). A cell surface labeling study indicated that the human cells expressed FGF receptor-3c, and the cells were found to contain FGF receptor-3c mRNA.

As a receptor ligand, the activity of an FGF-18 component or FGF-18 targeting composition can be determined using a silicon-based biosensor microphysiometer which measures the extracellular acidification rate or proton excretion associated with receptor binding and subsequent cellular responses. An exemplary device is the CYTOSENSOR Microphysiometer manufactured by Molecular Devices Corp. (Sunnyvale, Calif.). A variety of cellular responses, such as cell proliferation, ion transport, energy production, inflammatory response, regulatory and receptor activation, and the like, can be measured by this method (see, for example, McConnell et al., *Science* 257:1906 (1992), Pitchford et al., *Meth. Enzymol.* 228:84 (1997), Arimilli et al., *J. Immunol. Meth.* 212:49 (1998), and Van Liefde et al., *Eur. J. Pharmacol.* 346:87 (1998)). Moreover, the microphysiometer can be used for assaying adherent or non-adherent cells.

Since energy metabolism is coupled with the use of cellular ATP, any event that alters cellular ATP levels, such as receptor activation and the initiation of signal transduction, will cause a change in cellular acid section. By measuring extracellular acidification changes in cell media over time, therefore, the microphysiometer directly measures cellular responses to various stimuli, including FGF-18. The microphysiometer can be used to measure responses of an FGF-18 responsive eukaryotic cell, compared to a control eukaryotic cell that does not respond to FGF-18 polypeptide. FGF-18 responsive eukaryotic cells comprise cells into which a receptor for FGF-18 has been transfected to create a cell that is responsive to FGF-18, or cells that are naturally responsive to FGF-18, such as the various cells described above. FGF-18 modulated cellular responses are measured by a change (e.g., an increase or decrease in extracellular acidification) in the response of cells exposed to FGF-18, compared with control cells that have not been exposed to FGF-18.

In addition, a solid phase system can be used to characterize an FGF-18 component or FGF-18 targeting composition. For example, a polypeptide comprising an FGF-18 component can be immobilized onto the surface of a receptor chip of a commercially available biosensor instrument (BIACORE, Biacore AB; Uppsala, Sweden). The use of this instrument is disclosed, for example, by Karlsson, *Immunol. Methods* 145:229 (1991), and Cunningham and Wells, *J. Mol. Biol.* 234:554 (1993).

As an illustration, a polypeptide comprising an FGF-18 component is covalently attached, using amine or sulfhydryl chemistry, to dextran fibers that are attached to gold film within a flow cell. A test sample is then passed through the cell. If FGF receptor-3 is present in the sample, it will bind to the immobilized polypeptide, causing a change in the refractive index of the medium, which is detected as a change in surface plasmon resonance of the gold film. This system allows the determination of on- and off-rates, from which binding affinity can be calculated, and assessment of stoichiometry of binding.

In addition, the effect of FGF-18 components and FGF-18 targeting compositions can be verified in vivo. As an illustration, the activity of FGF-18 targeting compositions on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. As an illustration, murine models have been developed for numerous conditions, including multiple myeloma, thyroid carcinogenesis, and bladder carcinoma (see, for example, Kubota, *J. Cell. Biochem.* 56:4 (1994), Capen and Sagartz, *Lab. Anim. Sci.* 48:580 (1998), and Radl, *Pathol. Biol.* (Paris) 47:109 (1999)).

For example, mice are treated with a test composition either through daily injection of FGF-18 components, or FGF-18 targeting compositions, or a one time injection of recombinant adenovirus that expresses the FGF-18 component or FGF-18 targeting composition. Three days following this treatment, $10^5$ to $10^6$ tumor cells are implanted under the dorsal skin. Alternatively, the cells themselves may be infected with recombinant adenovirus, such as one expressing FGF-18 targeting compositions, before implantation so that the protein is synthesized at the tumor site or intracellularly, rather than systemically. As another alternative, the implanted tumor cells can be transiently transfected with expression vectors comprising nucleic acid molecules that encode FGF-18 components. Although the mice normally develop visible tumors within five days, the tumors are allowed to grow for a period of up to three weeks. Tumor size and body weight are carefully monitored throughout the experiment. At the time of sacrifice, the tumor is removed and weighed. The resected tissues are prepared for histopathological examination, immunohistochemistry, and in situ hybridization, using methods known in the art. The influence of the expressed polypeptide in question, e.g., FGF-18 targeting compositions, on the ability of the tumor to recruit vasculature and undergo growth or metastasis can thus be assessed.

5. Therapeutic Uses of FGF-18 Targeting Compositions

The present invention includes the use of FGF-18 targeting compositions, including FGF-18 conjugates and FGF-18 targeting fusion proteins to inhibit the proliferation of cells that express FGF receptor-3 or FGF receptor-2. These molecules can be administered to any subject in need of treatment, and the present invention contemplates both veterinary and human therapeutic uses. Illustrative subjects include mammalian subjects, such as farm animals, domestic animals, and human patients.

Chesi et al., *Nature Genet.* 16:260 (1997), have described a mutation in the protein kinase domain of FGF receptor-3 associated with multiple myeloma cells. The FGF receptor-3 gene appears to be upregulated due to a translocation, which brings the gene within 50 to 100 kb of strong IgH enhancers (Chesi et al., *Nature Genet.* 16:260 (1997); Chesi et al., *Blood* 92:3025 (1998)). Regardless of the role of FGF receptor-3 gene dysregulation in multiple myeloma development, the expressed FGF receptor-3 polypeptide provides a marker for therapeutic treatment. Accordingly, the present invention includes the treatment of multiple myeloma with FGF-18 targeting compositions.

The compositions described herein can be used to treat additional conditions. For example, achondroplasia, the most common form of dwarfism in man, is a dominant genetic disorder caused by a point mutation in the transmembrane region of FGF receptor-3 (see, for example, Wang et al., *Proc Nat'l Acad. Sci. USA* 96:4455 (1999)). The point mutation appears to cause a constitutive expression of FGF receptor-3 (Colvin et al., *Nature Genet.* 12:390 (1996); Deng et al., *Cell* 84:911 (1996)). Growth hormone administration provides one form of treatment for achondroplasia (Seino et al., *Acta Paediatr.* (Suppl.) 88:118 (1999)). FGF-18 targeting compositions can provide an additional therapeutic approach, which can be tested in achondroplastic dwarf mice, a murine model for testing treatment of the human disease (Wang et al., *Proc Nat'l Acad. Sci. USA* 96:4455 (1999)).

There are additional conditions that would benefit from the administration of FGF-18 targeting compositions. For example, Cappellen et al., *Nature Genetics* 23:18 (1999), describe the expression of constitutively activated FGF receptor-3 in common epithelial cancers, such as human bladder and cervix carcinomas. The present inventor found that an FGF-18-saporin conjugate specifically kills human osteosarcoma cells, while sparing fibroblasts. Moreover, studies by Onose et al., *Eur. J. Endocrinol.* 140:169 (1999), indicate that over-expression of FGF receptor-3 by human thyroid carcinoma cells can contribute to the malignant extension of carcinomas. Thus, FGF-18 targeting compositions can be used to treat conditions associated with FGF receptor-3, such as achondroplasia, osteosarcoma, and carcinomas.

Since FGF-18 also binds with FGF receptor-2, the compositions described herein can be used to treat conditions associated with this receptor. For example, Hughes, *Cardiovasc. Res.* 32:557 (1996), observed widespread co-expression of FGF receptor-1 and FGF receptor-2 in intimal smooth muscle cells, foam cells and the plaque microvasculature of simple and advanced atherosclerotic lesions. Accordingly, the present invention includes treatment for atherosclerosis with FGF-18 targeting compositions.

Generally, the dosage of administered FGF-18 targeting compositions will vary depending upon such factors as the subject's age, weight, height, sex, general medical condition and previous medical history. Typically, it is desirable to provide the recipient with a dosage of FGF-18 targeting composition, which is in the range of from about 1 pg/kg to 10 mg/kg (amount of agent/body weight of subject), although a lower or higher dosage also may be administered as circumstances dictate.

Administration of an FGF-18 targeting composition to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising FGF-18 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a molecule having FGF-18 binding activity (Potts et al., *Pharm. Biotechnol.* 10:213 (1997)).

A pharmaceutical composition comprising an FGF-18 targeting composition can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, an FGF-18 targeting composition and a pharmaceutically acceptable carrier are administered to a patient in a therapeutically effective amount. A combination of an FGF-18 targeting composition and a pharmaceutically acceptable carrier is said to be administered in a "therapeutically effective amount" if the amount administered is physiologically significant. An agent is physiologically significant if its presence results in a detectable change in the physiology of a recipient subject. For example, an agent used to treat multiple myeloma is physiologically significant if the agent's presence results in the inhibition of the growth of tumor cells. An inhibition of the progress of multiple myeloma or osteosarcoma may be indicated, for example, by a decrease in the number of tumor cells, decreased metastasis, a decrease in the size of a solid tumor, or increased apoptosis or necrosis of a tumor.

A pharmaceutical composition comprising an FGF-18 targeting composition can be furnished in liquid form, in an aerosol, or in solid form. Liquid forms are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified FGF-18 compositions, in which an FGF-18 component is linked with a polymer. Preferred FGF-18 polypeptides are soluble polypeptides. Typically, the polymer is water soluble so that the FGF-18 conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-($C_1$-$C_{10}$) alkoxy, or aryloxy derivatives thereof (see, for example, Harris, et al., U.S. Pat. No. 5,252,714). The polymer may be branched or unbranched. Moreover, a mixture of polymers can be used to produce FGF-18 conjugates.

FGF-18 conjugates used for therapy can comprise pharmaceutically acceptable water-soluble polymer moieties. Suitable water-soluble polymers include polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. An FGF-18 conjugate can also comprise a mixture of such water-soluble polymers.

One example of an FGF-18 conjugate comprises an FGF-18 moiety and a polyalkyl oxide moiety attached to the N-terminus of the FGF-18 moiety. PEG is one suitable polyalkyl oxide. As an illustration, FGF-18 can be modified with PEG, a process known as "PEGylation." PEGylation of FGF-18 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, FGF-18 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with an FGF-18 polypeptide. An example of an activated PEG ester is PEG esterified to N-hydroxysuccinimide. As used herein, the term "acylation" includes the following types of linkages between FGF-18 and a water soluble polymer: amide, carbamate, urethane, and the like. Methods for preparing PEGylated FGF-18 by acylation will typically comprise the steps of (a) reacting an FGF-18 polypeptide with PEG (such as a reactive ester of an aldehyde derivative of PEG) under conditions whereby one or more PEG groups attach to FGF-18, and (b) obtaining the reaction product(s). Generally, the optimal reaction conditions for acylation reactions will be determined based upon known parameters and desired results. For example, the larger the ratio of PEG:FGF-18, the greater the percentage of polyPEGylated FGF-18 product.

The product of PEGylation by acylation is typically a polyPEGylated FGF-18 product, wherein the lysine ε-amino groups are PEGylated via an acyl linking group. An example of a connecting linkage is an amide. Typically, the resulting FGF-18 will be at least 95% mono-, di-, or tri-pegylated, although some species with higher degrees of PEGylation may be formed depending upon the reaction conditions. PEGylated species can be separated from unconjugated FGF-18 polypeptides using standard purification methods, such as dialysis, ultrafiltration, ion exchange chromatography, affinity chromatography, and the like.

PEGylation by alkylation generally involves reacting a terminal aldehyde derivative of PEG with FGF-18 in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of FGF-18 monopolymer conjugates.

Reductive alkylation to produce a substantially homogenous population of monopolymer FGF-18 conjugate molecule can comprise the steps of: (a) reacting an FGF-18. polypeptide with a reactive PEG under reductive alkylation conditions at a pH suitable to permit selective modification of the α-amino group at the amino terminus of the FGF-18, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer FGF-18 conjugates, the reductive alkylation reaction conditions are those which permit the selective attachment of the water soluble polymer moiety to the N-terminus of FGF-18. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:FGF-18 need not be as large because more reactive groups are available. Typically, the pH will fall within the range of 3 to 9, or 3 to 6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to FGF-18 will generally be in the range of 1:1 to 100:1. Typically, the molar ratio of water-soluble polymer to FGF-18 will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther*. 59:636 (1996), Monkarsh et al., *Anal. Biochem*. 247:434 (1997)).

Polypeptide cytotoxins can also be conjugated with a soluble polymer using the above methods either before or after conjugation to an FGF-18 component. Soluble polymers can also be conjugated with FGF-18 targeting fusion proteins.

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method of inhibiting the proliferation of cells that express fibroblast growth factor (FGF) receptor-3 or FGF receptor-2, comprising administering a composition comprising an FGF-18 targeting composition to the cells, wherein said FGF-18-targeting composition comprises an FGF18 component and a cytoxin wherein said FGF18 component comprises a polypeptide having at least 95% sequence identity to SEQ ID NO:2.

2. The method of claim 1, wherein the administered composition is a pharmaceutical composition, and wherein the pharmaceutical composition is administered in a therapeutically effective amount to a subject that has a tumor, wherein the tumor comprises cells that express FGF receptor-3 or FGF receptor-2.

3. The method of claim 1, wherein the cells are selected from the group consisting of multiple myeloma cells, bladder carcinoma cells, cervix carcinoma cells, thyroid carcinoma cells, osteosarcoma cells, and intimal smooth muscle cells.

4. The method of claim 3, wherein the cells are multiple myeloma cells or osteosarcoma cells, and where the composition that is administered comprises a fibroblast growth factor (FGF)-18-saporin conjugate, wherein the cells express at least one of FGF receptor-3 or FGF receptor-2, and wherein the FGF-18-saporin conjugate comprises either amino acid residues 28 to 196 of SEQ ID NO:2, or amino acid residues 28 to 196 of SEQ ID NO:4.

5. The method of claim 4, wherein the cells are multiple myeloma cells.

6. The method of claim 4, wherein the cells are osteosarcoma cells.

7. The method of claim 4, wherein the FGF-18-saporin conjugate comprises amino acid residues 28 to 196 of SEQ ID NO:2.

8. The method of claim 7, wherein the FGF-18-saporin conjugate comprises amino acid residues 28 to 207 of SEQ ID NO:2.

9. The method of claim 8, wherein the FGF-18-saporin conjugate comprises the amino acid sequence of SEQ ID NO:2.

10. The method of claim 4, wherein the FGF-18-saporin conjugate comprises amino acid residues 28 to 196 of SEQ ID NO:4.

11. The method of claim 10, wherein the FGF-18-saporin conjugate comprises amino acid residues 28 to 207 of SEQ ID NO:4.

12. The method of claim 11, wherein the FGF-18-saporin conjugate comprises the amino acid sequence of SEQ ID NO:4.

13. A method of inhibiting the proliferation of osteosarcoma cells, comprising administering a composition that comprises a fibroblast growth factor (FGF)-18-saporin conjugate to the osteosarcoma cells, wherein the osteosarcoma cells express at least one of FGF receptor-3 or FGF receptor-2, and wherein the FGF-18-saporin conjugate comprises the amino acid sequence of SEQ ID NO:2.

14. A method of inhibiting the proliferation of multiple myeloma cells, comprising administering a composition that comprises a fibroblast growth factor (FGF)-18-saporin conjugate to the multiple myeloma cells, wherein the multiple myeloma cells express at least one of FGF receptor-3 or FGF receptor-2, and wherein the FGF-18-saporin conjugate comprises the amino acid sequence of SEQ ID NO:2.

15. The method of claim 1 wherein said FGF18 component consists of a polypeptide having at least 95% sequence identity to SEQ ID NO:2.

16. The method of claim 1 wherein said FGF18 component consists of amino acid residues 28 to 196 of SEQ ID NO:2.

17. The method of claim 1 wherein said FGF18 component consists of amino acid residues 28 to 196 of SEQ ID NO:2 with an amino-terminal methionine residue.

* * * * *

SEQUENCE LISTING

<160> NUMBER OF SEQ ID NOS: 5

<210> SEQ ID NO 1
<211> LENGTH: 917
<212> TYPE: DNA
<213> ORGANISM: Homo sapiens
<220> FEATURE:
<221> NAME/KEY: CDS
<222> LOCATION: (1)...(621)

<400> SEQUENCE: 1

```
atg tat tca gcg ccc tcc gcc tgc act tgc ctg tgt tta cac ttc ctg      48
Met Tyr Ser Ala Pro Ser Ala Cys Thr Cys Leu Cys Leu His Phe Leu
 1               5                  10                  15 ctg ctg tgc ttc cag gta cag gtg ctg gtt gcc gag gag aac gtg gac      96
Leu Leu Cys Phe Gln Val Gln Val Leu Val Ala Glu Glu Asn Val Asp
             20                  25                  30 ttc cgc atc cac gtg gag aac cag acg cgg gct cgg gac gat gtg agc     144
Phe Arg Ile His Val Glu Asn Gln Thr Arg Ala Arg Asp Asp Val Ser
         35                  40                  45 cgt aag cag ctg cgg ctg tac cag ctc tac agc cgg acc agt ggg aaa     192
Arg Lys Gln Leu Arg Leu Tyr Gln Leu Tyr Ser Arg Thr Ser Gly Lys
     50                  55                  60 cac atc cag gtc ctg ggc cgc agg atc agt gcc cgc ggc gag gat ggg     240
His Ile Gln Val Leu Gly Arg Arg Ile Ser Ala Arg Gly Glu Asp Gly
```

|  |  |  |  |  |  |  |  |  |  |  |  |  |  |  |  |
|---|---|---|---|---|---|---|---|---|---|---|---|---|---|---|---|
|  |  | 65 |  |  |  | 70 |  |  |  | 75 |  |  |  | 80 |  |

```
gac aag tat gcc cag ctc cta gtg gag aca gac acc ttc ggt agt caa      288
Asp Lys Tyr Ala Gln Leu Leu Val Glu Thr Asp Thr Phe Gly Ser Gln
                85                  90                  95 gtc cgg atc aag ggc aag gag acg gaa ttc tac ctg tgc atg aac cgc      336
Val Arg Ile Lys Gly Lys Glu Thr Glu Phe Tyr Leu Cys Met Asn Arg
            100                 105                 110 aaa ggc aag ctc gtg ggg aag ccc gat ggc acc agc aag gag tgt gtg      384
Lys Gly Lys Leu Val Gly Lys Pro Asp Gly Thr Ser Lys Glu Cys Val
        115                 120                 125 ttc atc gag aag gtt ctg gag aac aac tac acg gcc ctg atg tcg gct      432
Phe Ile Glu Lys Val Leu Glu Asn Asn Tyr Thr Ala Leu Met Ser Ala
    130                 135                 140 aag tac tcc ggc tgg tac gtg ggc ttc acc aag aag ggg cgg ccg cgg      480
Lys Tyr Ser Gly Trp Tyr Val Gly Phe Thr Lys Lys Gly Arg Pro Arg
145                 150                 155                 160 aag ggc ccc aag acc cgg gag aac cag cag gac gtg cat ttc atg aag      528
Lys Gly Pro Lys Thr Arg Glu Asn Gln Gln Asp Val His Phe Met Lys
                165                 170                 175 cgc tac ccc aag ggg cag ccg gag ctt cag aag ccc ttc aag tac acg      576
Arg Tyr Pro Lys Gly Gln Pro Glu Leu Gln Lys Pro Phe Lys Tyr Thr
            180                 185                 190 acg gtg acc aag agg tcc cgt cgg atc cgg ccc aca cac cct gcc          621
Thr Val Thr Lys Arg Ser Arg Arg Ile Arg Pro Thr His Pro Ala
        195                 200                 205 taggccaccc cgccgcggcc ctcaggtcgc cctggccaca ctcacactcc cagaaaactg    681
catcagagga atattttac atgaaaaata aggatttat tgttgacttg aaaccccga       741 tgacaaaaga ctcacgcaaa gggactgtag tcaacccaca ggtgcttgtc tctctctagg    801
aacagacaac tctaaactcg tccccagagg aggacttgaa tgaggaaacc aacactttga    861
gaaaccaaag tcctttttcc caaggttct gaaaaaaaa aaaaaaaaa ctcgag           917
```

<210> SEQ ID NO 2
<211> LENGTH: 207
<212> TYPE: PRT
<213> ORGANISM: Homo sapiens

<400> SEQUENCE: 2

```
Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140
```

```
Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
            165                 170                 175

Arg Tyr Pro Lys Gly Gln Pro Glu Leu Gln Lys Pro Phe Lys Tyr Thr
        180                 185                 190

Thr Val Thr Lys Arg Ser Arg Arg Ile Arg Pro Thr His Pro Ala
        195                 200                 205

<210> SEQ ID NO 3
<211> LENGTH: 1023
<212> TYPE: DNA
<213> ORGANISM: Mus musculus
<220> FEATURE:
<221> NAME/KEY: CDS
<222> LOCATION: (1)...(624)

<400> SEQUENCE: 3 atg tat tca gcg ccc tcc gcc tgc act tgc ctg tgt tta cac ttt cta     48
Met Tyr Ser Ala Pro Ser Ala Cys Thr Cys Leu Cys Leu His Phe Leu
1               5                   10                  15 ctg ctg tgc ttc cag gtt cag gtg ttg gca gcc gag gag aat gtg gac     96
Leu Leu Cys Phe Gln Val Gln Val Leu Ala Ala Glu Glu Asn Val Asp
            20                  25                  30 ttc cgc atc cac gtg gag aac cag acg cgg gct cga gat gat gtg agt    144
Phe Arg Ile His Val Glu Asn Gln Thr Arg Ala Arg Asp Asp Val Ser
        35                  40                  45 cgg aag cag ctg cgc ttg tac cag ctc tat agc agg acc agt ggg aag    192
Arg Lys Gln Leu Arg Leu Tyr Gln Leu Tyr Ser Arg Thr Ser Gly Lys
    50                  55                  60 cac att caa gtc ctg ggc cgt agg atc agt gcc cgt ggc gag gac ggg    240
His Ile Gln Val Leu Gly Arg Arg Ile Ser Ala Arg Gly Glu Asp Gly
65                  70                  75                  80 gac aag tat gcc cag ctc cta gtg gag aca gat acc ttc ggg agt caa    288
Asp Lys Tyr Ala Gln Leu Leu Val Glu Thr Asp Thr Phe Gly Ser Gln
                85                  90                  95 gtc cgg atc aag ggc aag gag aca gaa ttc tac ctg tgt atg aac cga    336
Val Arg Ile Lys Gly Lys Glu Thr Glu Phe Tyr Leu Cys Met Asn Arg
            100                 105                 110 aaa ggc aag ctc gtg ggg aag cct gat ggt act agc aag gag tgc gtg    384
Lys Gly Lys Leu Val Gly Lys Pro Asp Gly Thr Ser Lys Glu Cys Val
        115                 120                 125 ttc att gag aag gtt ctg gaa aac aac tac acg gcc ctg atg tct gcc    432
Phe Ile Glu Lys Val Leu Glu Asn Asn Tyr Thr Ala Leu Met Ser Ala
    130                 135                 140 aag tac tct ggt tgg tat gtg ggc ttc acc aag aag ggg cgg cct cgc    480
Lys Tyr Ser Gly Trp Tyr Val Gly Phe Thr Lys Lys Gly Arg Pro Arg
145                 150                 155                 160 aag ggt ccc aag acc cgc gag aac cag caa gat gta cac ttc atg aag    528
Lys Gly Pro Lys Thr Arg Glu Asn Gln Gln Asp Val His Phe Met Lys
                165                 170                 175 cgt tac ccc aag gga cag gcc gag ctg cag aag ccc ttc aaa tac acc    576
Arg Tyr Pro Lys Gly Gln Ala Glu Leu Gln Lys Pro Phe Lys Tyr Thr
            180                 185                 190 aca gtc acc aag cga tcc cgg cgg atc cgc ccc act cac ccc ggc tag    624
Thr Val Thr Lys Arg Ser Arg Arg Ile Arg Pro Thr His Pro Gly *
        195                 200                 205 gtccggccac actcacccc ccagagaact catcagagg aatatttta catgaaaaat       684 aaggaagaat ctctattttt gtacattgtg tttaaaagaa gacaaaaact gaacctaaag    744
```

```
tcttgggagg aggggcgata ggattccact gttgacctga acccccatgac aaaggactca    804 cacaagggga ccgctgtcaa cccacaggtg cttgcctctc tctaggaggt gacaattcaa    864
aactcatccc cagaggagga cttgaacgag gaaactgcga gaaaccaaag tcctttcccc    924
ccaaaggttc tgaaagcaaa caaaaaaaaa aaaaaaaaa aaaaaaaaaa aaaaaaaaaa    984
aaaaaaaaaa aaaaaaaaaa gggcggccgc tctagagga                          1023
```

```
<210> SEQ ID NO 4
<211> LENGTH: 207
<212> TYPE: PRT
<213> ORGANISM: Mus musculus

<400> SEQUENCE: 4

Met Tyr Ser Ala Pro Ser Ala Cys Thr Cys Leu Cys Leu His Phe Leu
 1               5                  10                  15

Leu Leu Cys Phe Gln Val Gln Val Leu Ala Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Ala Glu Leu Gln Lys Pro Phe Lys Tyr Thr
            180                 185                 190

Thr Val Thr Lys Arg Ser Arg Arg Ile Arg Pro Thr His Pro Gly
        195                 200                 205
```

```
<210> SEQ ID NO 5
<211> LENGTH: 621
<212> TYPE: DNA
<213> ORGANISM: Artificial Sequence
<220> FEATURE:
<223> OTHER INFORMATION: This degenerate sequence encodes the amino acid
      sequence of SEQ ID NO:2.
<220> FEATURE:
<221> NAME/KEY: variation
<222> LOCATION: (1)...(621)
<223> OTHER INFORMATION: N is any nucleotide.

<400> SEQUENCE: 5
atgtaywsng cnccnwsngc ntgyacntgy ytntgyytnc aytthytnyt nytntgytty     60
cargtncarg tnytngtngc ngargaraay gtngayttym gnathcaygt ngaraaycar    120
acnmgngcnm gngaygaygt nwsnmgnaar carytnmgny tntaycaryt ntaywsnmgn    180
acnwsnggna arcayathca rgtnytnggn mgnmgnathw sngcnmgngg ngargayggn    240
```

-continued

| | |
|---|---|
| gayaartayg cncarytnyt ngtngaracn gayacnttyg gnwsncargt nmgnathaar | 300 |
| ggnaargara cngarttyta yytntgyatg aaymgnaarg gnaarytngt nggnaarccn | 360 |
| gayggnacnw snaargartg ygtnttyath garaargtny tngaraayaa ytayacngcn | 420 |
| ytnatgwsng cnaartayws nggntggtay gtnggnttya cnaaraargg nmgnccnmgn | 480 |
| aarggnccna aracnmgnga raaycarcar gaygtncayt tyatgaarmg ntayccnaar | 540 |
| ggncarccng arytncaraa rccnttyaar tayacnacng tnacnaarmg nwsnmgnmgn | 600 |
| athmgnccna cncayccngc n | 621 |